United States Patent [19]

Winkelhake

[11] Patent Number: 4,720,459

[45] Date of Patent: Jan. 19, 1988

[54] MYELOMAS FOR PRODUCING HUMAN/HUMAN HYBRIDOMAS

[75] Inventor: Jeffrey L. Winkelhake, Emeryville, Calif.

[73] Assignee: Medical College of Wisconsin Research Foundation, Inc., Milwaukee, Wis.

[21] Appl. No.: 701,921

[22] Filed: Feb. 14, 1985

[51] Int. Cl.[4] .................. C12N 5/00; C12N 15/00; C12R 1/91

[52] U.S. Cl. .................. 435/240.2; 435/172.2; 435/948; 435/240.27; 935/100

[58] Field of Search .................. 435/172.2, 240, 241, 435/948; 935/100

[56] References Cited

U.S. PATENT DOCUMENTS

| | | | |
|---|---|---|---|
| 4,451,570 | 5/1984 | Royston et al. | 435/948 |
| 4,594,325 | 6/1986 | Lundak | 435/948 |
| 4,608,337 | 8/1986 | Croce | 935/100 |

OTHER PUBLICATIONS

C. Croce et al., 288 Nature, 488–89 (1980).
N. Chiorazzi et al., 156, J. Exp. Med., 930–935 (1982).
R. Levy et al., 75 Proc. Natl. Acad. Sci., USA, 2411–2415 (1978).
J. Schwaber et al., 244, Nature, 444–47 (1973).
J. Schlom et al., 77 Proc. Natl. Acad. Sci., USA, 6841–6845 (1980).
H. Lane et al., 155 J. Exp.'l Med., 333–338 (1982).
N. Teng et al., 80 Proc. Natl. Acad. Sci. USA, 7308–7312 (1983).
Zurawski et al., 199 Science, 1439–1441 (1978).
Yoshie et al., 56 Cell., 305–316 (1980).
G. Kohler et al., 6 Eur. J. Immunol., 511–519 (1976).
L. Strike et al., 132 J. Immunol., 1798–1803 (1984).
M. Hoffmann, 77 Proc. Natl. Acad. Sci. USA, 1139–1143 (1980).
J. Delfraissy et al., 118 J. Immunol., 630–635 (1977).
G. Astaldi et al., 128 J. Immunol., 2539–2542 (1982).
M. Goodman et al., 78 Proc. Natl. Acad. Sci. USA, 7604–7608 (1981).
M. Goodman et al., 128 J. Immunol., 2399–2404 (1982).
E. Stanbridge, 260 Nature, 17–20 (1976).
J. Winkelhake et al., 259 J. Bio. Chem., 2171–2178 (1984).
S. Avrameas, 8 Scand. J. Immunol., 7–23 (1978).
D. Kaplan et al., 132 J. Immunol., 9–11 (1984).
K. Brunner, In Vitro Methods in Cell Mediated and Tumor Immunity, Bloom and David Eds, Academy Press, 423–428 (1976).
J. Inman et al., 8 Bio. Chem., 4074–4082 (1969).
A. Cunningham et al., 14 Immunol., 599–601 (1976).
J. Garvey et al., Methods in Immunology, 360–371 (1977).
Hunter et al., "Antibacterial Activity of a Human Monoclonal Antibody to Haemophilus Influenza Type B Capsular Polysaccharide", Lancet 2, pp. 798–799 (1982).
Pickering et al., "A Human Myeloma Cell Line that does not Express Immunoglobulin but Yields a High Frequency of Antibody . . . ", Journal of Immunology 123(1), pp. 406–412 (1982).
Levy et al., "Further Characterization of the WI-L1 and WI-L2 Lymphoblastoid Lines", Journal of the National Cancer Institute 46(3), pp. 647–652 (1971).
Abrams et al., "Determination of the Optimal Human Cell Lines for Development of Human Hybridomas", Journal of Immunology 131(3), pp. 1201–1204 (1983).
ATCC Catalogue of Cell Lines and Hybridomas, 5th ed., pp. 85 and 152 (1985).

*Primary Examiner*—John E. Tarcza
*Attorney, Agent, or Firm*—Quarles & Brady

[57] ABSTRACT

Human myeloma fusing lines and human/human hybridomas produced therefrom are disclosed. In one embodiment, the myeloma cell line is HAT sensitive, does not secrete detectable levels of Epstein-Barr virus EBNA-I protein, and does not secrete or elaborate detectable levels of myeloma immunoglobulin. The myeloma cell line and resulting hybridoma are stable over time, and thus permit production of commercial quantities of human monoclonal antibody.

3 Claims, No Drawings

MYELOMAS FOR PRODUCING HUMAN/HUMAN HYBRIDOMAS

This work was supported in part by grants from the United States Public Health Service, NIH, RO1-AI17977, and the Arthritis Foundation, Wisconsin Affiliate.

BACKGROUND OF THE INVENTION

A. Field Of The Invention

This invention relates to monoclonal antibody technology. More specifically, it relates to myelomas which can be used to create human/human hybridomas.

B. Description Of The Art

The pioneering work of G. Kohler and C. Milstein, 6 Eur. J. Immunol. 511-519 (1976) (the disclosure of this article and of all other articles referred to herein are incorporated herein as if fully set forth) spawned monoclonal antibody research. The goal of this research was the development of ways to obtain virtually unlimited quantities of pure antibody with a single specificity.

Antibodies are protein molecules produced by animals to protect them against invasion by bacteria, parasites, viruses, and other foreign substances. For nearly any foreign substance ("antigen"), there are antibodies able to recognize only that chemical structure. The human body makes millions of different genetically programmed antibody molecules, each recognizing a different target or chemical structure. As normal components of our blood stream, antibodies are extremely useful to medicine, science, and industry, because of their specificity in recognizing and physically binding to substances in the human body.

Prior to the work of Kohler and Milstein, antibodies were produced in infected animals and purified from their blood. However, this method had significant limitations. The antibody quality changed with each lot. Further, even using large animals, there was a practical limitation to the quantity obtained.

More importantly, the blood of any animal contains the sought-after antibody along with millions of other antibodies, each recognizing a different structure. Thus, conventionally-produced antibodies had multiple specificities and were difficult or impossible to use for many applications.

The procedure Kohler and Milstein used for producing monoclonal antibodies began with the injection of the antigen or target chemical into a mouse. When lymphocytes began proliferating, the lymphocyte-rich spleen was taken from the mouse. Among the many lymphocytes were a few with the antibody molecules of the desired specificity. The entire population of lymphocytes obtained from the spleen was then mixed with mouse "myeloma" (bone marrow tumor) cells.

Like most cancer cells, myeloma cells can survive indefinitely when grown in cultures. Next, the myeloma cells and lymphocytes were fused, most commonly by adding polyethlyene glycol. The goal was a "hybridoma," a cell that combined the antibody producing capability of lymphocytes with the survival capability of myeloma cells. Somewhere among the hundreds of million cells treated with PEG, there were usually a few hybridomas producing the desired antibody.

These cells were normally found and separated in a three step process of selection, screening, and cloning. Selection first identifies only the properly fused hybridoma cells. This is readily achieved (because unfused lymphocytes will naturally die after a few days in culture). The remaining task in selection is to eliminate myeloma cells which have not fused with lymphocytes.

To achieve this, the original myeloma cells are usually genetically altered to lack the entire enzyme thymidine kinase (TK). When cells lacking TK are grown in a special culture fluid, HAT, they die. However, if the myeloma fuses with a normal lymphocyte, the lymphocyte provides the TK enzyme, and the hybridoma cell grows.

Once properly fused hybridomas have been selected, they are screened for the single hybridoma cell that is producing the desired antibody molecule. The hybridoma cells are grown in small colonies, each in a separate well of a culture dish. Several techniques are used to identify a hybridoma producing the right antibody. One, radioimmunoassay, is widely used. The target antigen is chemically bound to the bottoms of small wells in a plastic tray. A little culture fluid from a well containing hybridoma colonies is added to one of the antigen-containing wells. Cultures with hybridomas secreting the desired antibody can be identified because the antibody will bind to the antigen in the dish and all others will be washed away.

At this point, a radioactively labelled reagent that specifically reacts with antibody molecules (often another antibody specific for antibody proteins) is added. After an appropriate incubation, the wells are washed again. Finding the desired monoclonal colony is simply a matter of locating the radioactive wells.

The final step is to ensure that all cells in the culture really are a clonal population. Cells are usually diluted so that only one cell is deposited into a culture vessel. The single cell divides, producing a clone of identical hybridoma cells. The antibody produced by these cells is a monoclonal antibody with the desired specificity. Because the hybridoma cell line is virtually immortal, it can be used essentially forever to produce its particular antibody, in mass quantities.

Unfortunately, the vast majority of cell hybridization products now available are rodent monoclonal antibodies. These have been used to locate, quantify and purify molecules, to study molecular architectures and to diagnose and treat diseases both in vitro and in vivo. The most useful application of monoclonal antibodies promises to be the clinical treatment of humans; but here the use of rodent antibodies introduces the problem of a host immune response against the foreign protein (serum sickness). In addition, some antigens in human tissue lack immunogencity in xenogeneic systems, and many human diseases involving autoantibodies rely on the patient to make an immune response. Thus, it can be seen that a need has existed for human counterparts for rat monoclonal antibodies.

Initial attempts at generating immortal human versions involved the fusion of human lymphocytes with mouse myeloma cells. This approach was unsuccessful because the hybrids preferentially lost human chromosomes, produced mouse myeloma protein, or did not express the Ig producing genes.

Recently, this approach was improved by producing a mouse:human heteromyeloma line which is reportedly capable of forming stable "tribrid" human immune B lymphocytes. However, the problem of chromosomal exclusion with such a hybrid is still very real, and myeloma protein produced by the cell complicates purification and lowers efficiency.

A very different alternative approach, transformation of antigen-primed B lymphocytes by Epstein-Barr virus (EBV) led to some initial success, but these cultures yielded low levels of specific antibody and tended to be unstable after time in culture.

Combining approaches, several investigators fused EBV-transformed human myeloma cell lines with antigen-primed human B lymphocytes. Resulting hybrids synthesize their original myeloma protein, monoclonal antibody and permuted molecules derived from fusion partners. This is an unsatisfactory solution because of the safety problems involved in the use of Eptein-Barr virus, and the separation problems caused by the presence of the myeloma protein and the associated permuted molecules.

Simply having an ideal fusion partner is not the only obstacle to the production of human/human hybridomas. It is also important to have a source of a large number of active, immune human B lymphocytes as the gene source for the human/human hybridomas. There are two routes of immunization, namely in vivo (in the body) and in vitro (in the test tube). The former occurs naturally in pathologic conditions, during infections or by vaccinations, but normal immunizations of humans with certain interesting antigens can be ruled out due to serious ethical problems. In vitro immunization is not without its attendant problems.

In vitro immunization requires a cell source, usually a spleen, thymus, synovial fluids, gut lymphocytes, or peripheral blood lymphocytes ("PBLs"). PBLs are not very active mitotically, and only about 30% of the leukocytes from normal peripheral blood are B lymphocytes. Thus, investigators have used a mitogen such as pokeweed or lipopolysaccharide to stimulate PBLs - thereby increasing the number of functional hybrids. This resulted in some success with the IgM-producing lymphocytes, but the IgG-producing lymphocytes which are of greater interest do not respond well to this approach. Thus, the methodologies of human lymphocyte hybridization did not include a good human/human hybridoma myeloma fusion partner, or a good source of active human B cells producing IgG antibodies of any desired specificity.

SUMMARY OF THE INVENTION

In one aspect of the invention, there is provided a human myeloma cell line which does not secrete detectable levels of EBNA-1 antigen from Epstein-Barr virus or detectable levels of myeloma immunoglobulin. The cell line is capable of fusing with human lymphocytes to form human/human hybridomas that produce antibodies. In an especially preferred embodiment, the myeloma cell line is HAT-sensitive and is a human lymphoblastoid.

The preferred cell line (HuNS1) is also an EMS induced variant of the GM4672 (ATCC) cell line. HuNS1 is deposited with the American Type Culture Collection in Rockville, Maryland with ATCC number CRL 8644, and will be made available upon the issuance of this patent in accordance with U.S. patent law and such other foreign patent laws as may apply. The availability of this culture is not meant as a license.

As described hereinafter, in order to provide a suitable supply of active human B lymphocytes, the cells are treated so as to kill off T-suppressor cells and keep available T-helper cells. This stimulates IgG antibody production.

The objects of the invention therefore include:

(a) Providing a human myeloma cell of the above kind which is stable, clonable, HAT-sensitive, EBNA negative, and Ig non-producing; and (b) Providing human/human hybridomas produced from myelomas of the above kind.

These and other objects and advantages of the invention will appear from the description which follows. While the preferred embodiments of the invention will be discussed below, they are not meant to be the exclusive embodiments covered by the claims. Thus, the claims should be looked to for assessing the scope of the invention.

DESCRIPTION OF THE PREFERRED EMBODIMENT

Overview

Starting with the GM4672 myeloma (ATCC) cell line, (see, C. Croce, 288 Nature 488-489 (1980), one uses a combination of chemical mutagenesis and culture selection techniques to isolate variants which have all of the desired properties. It is believed that a similar approach can be applied with other cell lines. We then used a novel approach to in vitro immunization of human PBLs which includes depletion of PBL total T cells or T-suppressor activity with either anti-sheep erythrocyte rosetter receptor or anti-human T-suppressor monoclonal antibodies. We then reconstituted effective T:B cell ratios prior to vaccination in culture with immunogen, mitogens, a polyclonal B cell stimulator, and IL-2 (T-cell growth factor). Model experiments are described for the de novo production of monoclonal antibidies to several haptens (the "antigens") of intial interest. Abbreviations used: BDB, bis-diazitized benzidine; BSA, bovine serum albumin; ELISA, enzyme-linked, immunosorbent assay; Ig, immunoglobulin(s); MAb, monoclonal antibody; PBS, 0.1 M phosphate-buffered saline pH 7.4.

Cell Line Medium: RPMI1640 supplemented with 15% FBS, 2 mM L-gln, 12 mM glc., 10 mM HEPES, 1 mM pyruvate, 0.02 mM 2-amino-6 -methylmercaptopurine (omitted for Hybrid Medium); HAT medium is hybrid media supplemented with 10 mM hypoxanthine, $3.63 \times 10^{-7}$ mM aminopterin and $1.6 \times 10^{-3}$ mM thymidine.

Creation Of The HuNS1 Variant Of GM4672

Step gradients of ficoll-hypaque were prepared from 7% ficoll (Pharmacia), 11% sodium diatrizoate (Winthrop Labs) by the addition of water to obtain the following densities 1.08, 1.07, 1.06, 1.05, 1.04, 1.02 g/cm$^2$. These gradients were allowed to stand at room temperature for 5 hrs to develop a continuous gradient before $10 \times 10^6$ GM4672 cells (Genetic Mutant Cell Repository, ATCC) in 2 ml RPMI 1640 (MA Bioproducts) was applied to the top. The gradients were then centrifuged at 1,000 rpm for 20 min. Cells from the low density fraction were cloned by limiting dilution on feeder layers consisting of the GM4672 cell line lethally irradiated at $10^5$/ml (5,000 R gamma) in 96-well, flat bottom plates (Costar). Production of immunoglobulin was assessed at 4-6 wks by ELISA. None of the subclones expressed IgG2 myeloma protein on their surfaces although all secreted ca. 25 µg/ml/24 hr culture of intact myeloma protein. Thus, anti-gamma 2 antibody and C had no selective advantage and to effect mutations in the active immunoglobulin producing genes one of the subclones (GM4672.W) was grown to confluence ($10^6$/ml) and exposed for 12 hrs to 200, 300, or 400 µg/ml EMS (ethyl methane sulfonate, Sigma). These doses were previously used to induce HAT sensitive mutants of murine and human myelomas. See G. Kohler et al. 6 Eur. J. Immunol. 511-519 (1976). Cells were recovered from the EMS containing medium and viable cells isolated on Histopaque (Sigma).

After initial trials it was determined that an additional 3 days incubation in cell culture medium to allow for delayed cell death due to either drug toxicity or lethal mutagenesis prior to cloning by limiting dilution greatly enhanced the cloning efficiency of the mutagenized cells. At that time cells were again isolated on Histopaque and they were cloned (and are maintained) in cell line medium with 2-amino, 6-methylmercaptopurine (Sigma). See also J. Dilley 75 P.N.A.S. USA 2411-2415 (1978). Cloning is accomplished on feeder layers of (5,000 R gamma) irradiated GM4672.W cells in 96 well plates with assay for immunoglobulin production at about 4 weeks.

By this procedure, four nonsecreting subclones (called HuNS1-HuNS4) were isolated and assayed for mycoplasma infection by the method of Kaplan et al., 132 J. Immunol 9-11 (1984) and for the presence of EBNA (evidence for Epstein Barr Virus). Mature cultures were also surveyed for the presence of any virus particles by electron microscopy (performed after glutaraldehyde fixation, uranyl acetate/lead citrate staining using a Philips EM400). All clones were mycoplasma free and two clones, HuNS1 and HuNS4 were Ig negative by ELISA (i.e., produce less than 10 ng/24 hr) and EBNA negative. HuNS1 was utilized for the studies described here and has remained stable with bi-annual subcloning for two years.

Depletion/Reconstitution of T Cell Subsets In PBL

Normal human PBL were isolated from individual buffy coats of fresh units of citrated whole blood or by leukophoresis. After sitting overnight at 25°, cells were diluted 1:4 with RPMI 1640 and leukocytes were isolated on Histopaque (Sigma) and rinsed twice with 40 ml volumes of RPMI 1640.

PBL were depleted of $T_S$, $T_H$, or total T-rosette receptor subpopulations using murine monoclonal antibodies OKT8, OKT4 (Orthodiagnostics) and ASR-1 (Abbott Laboratories) respectively with low tox rabbit C (Accurate Chem. and Scientif. Corp.) at dilutions determined optimal in a Na51CrO4—release assay. K. T. Brunner et al., In Vitro In Cell Mediated & Tumor Immunity, (B. Blocru & T. Davies, ed.) Acad. Press pp. 423-428 (1976). After incubating $10^6$ cells/ml with the appropriate dilution of monoclonal antibodies for 30 min the adding C for 60 min at 37° C., cells were reisolated on Histopaque.

For reconstituting T depleted PBL two approaches were taken. First an autochthonous, untreated sample was irradiated (5,000 rads gamma) and added to OKT-8 or OKT4-depleted B cells. Alternately, total T depleted B cells (PBLs treated with ASR-1) were reconstituted with untreated PBL to provide 50% of the original T cells and about 200% of the original B cells. Irradiation prevents T cells from proliferating in response to PWM but does not prevent release of soluble B-cell stimulators while reconstitution is designed to create a B:T cell ratio of about 50:50.

In Vitro Immunizations.

In vitro immunizations were accomplished by incubating cells ($0.5 \times 10^6$/ml) in 6-well cluster dishes in immunization media: consisting of hybrid media without FBS supplemented with 20% human AB serum (heat inactivated), 10 µl/ml of a 50% suspension of hapten-polyacrylamide beads, 10 µg/ml hapten conjugated to porcine gamma globulin carrier (generally 12-20 moles hapten per mole carrier), 300 µM 8-mercaptoguanosine, 1 µl/ml pokeweed mitogen (Gibco stock) and 1.0 mM insulin. Biogel P30 (100-200 mesh) polyacrylamide beads were derivatized with diethylamine heating 1 g P30 in 30 ml ethylenediamine at 90° for 40 min (J. K. Inman et al. 8 Biochem 4074-4092 (1969)). Beads were then derivatized with $DNBSO_3=$ or FITC as described for the TNP hapten J. F. Delfraissez 18 J. Immunol 630-635 (1977) with derivatization ranging from 30 to 60 hapten groups/bead depending upon the hapten.

Continuous slow rocking of incubation mixtures was followed on day 2 by the addition of one-half volume of fresh immunization medium (excluding new immunogen and 1 µl/ml PWM) and analysis/fusion on day 6. Average cell viability at this time was 78±5%. In vitro responsiveness was assessed by direct and indirect hemolytic plaque assay using hapten-coated sheep erythrocytes (sRBC) in a Cunningham modification, A. T. Cunningham, 14 Immunol 599-601 (1976), of the Jerne plaque assay.

Cell Fusions/Cloning

In vitro immunized PBLs were isolated again on Histopaque to remove Ag-beads and dead cells, rinsed with RPMI 1640 and incubated with rinsed HuNS-1 cells at a ratio of 1 to 5-10 at 37° for a 2 min period during which time 1.0 ml 40% PEG1240 was added dropwise with swirling. A second 2 min incubation with gentle swirling was followed by the addition of 1.0 ml RPMI 1640 over a 1 min period, 8 ml RPMI 1640 over the next 3 min and gentle pelleting of cells. Pellets were resuspended in 20 ml hybrid medium (J. Dilley et al. 75 Proc. Nat. Acad. Sci. USA 2411-1415 (1978)) and plated into four 96-well cluster dishes (50 µl/well).

After incubation for 48 hrs, one-half of the media was aspirated and replaced with HAT media daily for the next four days and on day 7. Normal tissue culture media was then added in a similar fashion (one-half vol/day) during days 10-12, and then every 3 days while hybrids were allowed to grow (1 to 2 more weeks). After 3-6 weeks (upon evidence of clone growth) PWM was added to culture media at 1:10,000 final dilution of stock until clones grew to be split to 48 well dishes. Positive wells were assessed for Ig and then specific antibody production. Some anti-hapten antibodies were also assessed by direct hemagglutination of $DNP_{12}$-BSA conjugated to sheep erythrocytes with bis-diazotized benzidine (BDB).

TESTING OF ANTIBODIES

Antibody specificities, class and subclass were determined using ELISAs during hybrid selection. Basically, all such assays were performed using NUNC 96 well Immunlon plates (Dynatech) pre-incubated with coating buffer (0.1 M carbonate: bicarbonate, pH 9.6, 0.02% $NaN_3$) for 2 hrs followed by coating with either antigen or with F(ab')$_2$ fragments of goat anti human K/λ (Cappel Laboratories) at 4° overnight. The following day, plates were washed with PBS incubated with 1% BSA in PBS and washed again. Samples and controls (50 μl each) were applied for 60 min at room temperature with gentle rocking. Wells were then rinsed four times with solution A (PBS, pH 7.2 with 1.5 mM MgCl₂, 2.0 mM B-mercaptoethanol, 0.05% Tween 20 and 0.05% NaN₃). A dilution of stock, second antibody F(ab')2-conjugated with B-galactosidase as described previously S. Avameas, Scand. J. Immunol. 7-23 (1978) was then applied (50 μl for 2 hrs, room temperature with rocking), followed by 4 more washed with soln.A. Substrate (PNP-B-D-galactoside from Sigma) was added at 1.0 mg/ml (50 μl/well) in solution B (0.05 M sodium phos. pH 7.2, 1.5 mM MgCl₂ and 100 mM B-mercaptoethanol) for approximately 1 hr. Reactions were terminated by the addition of 50 μl 0.5 M Na₂CO₃ and read in an ELISA plate scanner (Dynatech) within 24 hrs. If not assessed immediately, plates were maintained at 4° C. until scanning.

Thus, the present invention provides a human myeloma useful for the creation of a wide range of human/human hybridomas. The myeloma is EBV negative and myeloma Ig protein negative so that monoclonal antibody produced is not contaminated or interfered with. The myeloma is stable over time, as are the hybridomas it creates. The myeloma is also HAT sensitive so that it can be selected out.

While specific preferred embodiments have been described above, many other variations are meant to be within the scope of the claims. Thus, the antigen need not be a hapten. It could be any other antigen that antibodies recognize. Also, the many other myeloma cell lines could be designed that have the specified characteristics. Thus, the scope of the invention is to be judged by the claims which follow.

I claim:

1. A human myeloma having the identifying characteristics of the myeloma deposited with ATCC designation CRL 8644.

2. A human myeloma cell which does not secrete detectable levels of EBNA-I protein from Epstein-Barr virus, does not secrete detectable levels of myeloma immunoglobulin, and is capable of fusing with a human lymphocyte to form a human/human hybridoma that can support continuous predetermined antibody production of antibodies, the cell being derived from GM4672.

3. A cell capable of producing a single specie of human antibody, comprising:
a myeloma dervied human/human hybridoma which can produce said human antibody, yet does not secrete detectable levels of myeloma immunoglobulin other than said single specie of antibody, not detectable levels of Epstein-Barr virus EBNA-1 protein, and does not produce non-human antibody, the hybridoma being derived from GM4672.

* * * * *

UNITED STATES PATENT AND TRADEMARK OFFICE
CERTIFICATE OF CORRECTION

PATENT NO. : 4,720,459
DATED : January 19, 1988
INVENTOR(S) : Jeffrey L. Winkelhake It is certified that error appears in the above—identified patent and that said Letters Patent is hereby corrected as shown below:

Column 8, line 25 "not" should read --nor--

Signed and Sealed this

Thirty-first Day of May, 1988

*Attest:*

DONALD J. QUIGG

*Attesting Officer*   *Commissioner of Patents and Trademarks*